(12) United States Patent
Elliott et al.

(10) Patent No.: US 7,122,177 B2
(45) Date of Patent: *Oct. 17, 2006

(54) PREPARATION AND XENOTRANSPLANTATION OF PORCINE ISLETS

(75) Inventors: Robert Bartlett Elliott, Auckland (NZ); Riccardo Calafiore, Perugia (IT); Gusseppe Basta, Perugia (IT)

(73) Assignee: Diabcell PTY Ltd., Parkside (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/857,325

(22) PCT Filed: Jan. 19, 2001

(86) PCT No.: PCT/NZ01/00006

§ 371 (c)(1),
(2), (4) Date: Feb. 14, 2002

(87) PCT Pub. No.: WO01/52871

PCT Pub. Date: Jul. 26, 2001

(65) Prior Publication Data

US 2003/0044391 A1 Mar. 6, 2003

(30) Foreign Application Priority Data

| Jan. 20, 2000 | (NZ) | 502473 |
|---|---|---|
| Jan. 20, 2000 | (NZ) | 502474 |
| Jan. 20, 2000 | (NZ) | 502475 |
| Jan. 20, 2000 | (NZ) | 502476 |
| Feb. 11, 2000 | (NZ) | 502826 |
| May 12, 2000 | (NZ) | 504520 |
| May 12, 2000 | (NZ) | 504521 |
| May 12, 2000 | (NZ) | 504522 |
| May 12, 2000 | (NZ) | 504523 |
| Aug. 10, 2000 | (NZ) | 506287 |
| Aug. 15, 2000 | (NZ) | 506337 |
| Nov. 2, 2000 | (NZ) | 507961 |

(51) Int. Cl.
*A01N 63/00* (2006.01)
*C12N 5/00* (2006.01)

(52) U.S. Cl. .................. 424/93.1; 435/325
(58) Field of Classification Search ............ 435/325, 435/375, 376, 378, 379, 381; 424/93.1, 93.7
See application file for complete search history.

(56) References Cited

U.S. PATENT DOCUMENTS

| 4,850,993 A * | 7/1989 | Champion et al. .......... 604/408 |
| 5,389,535 A | 2/1995 | Aebischer et al. |
| 5,516,681 A | 5/1996 | Naughton et al. |
| 5,550,050 A | 8/1996 | Holland et al. |
| 5,561,108 A * | 10/1996 | Tsay et al. .............. 514/12 |
| 5,573,528 A | 11/1996 | Aebischer et al. |
| 5,762,926 A | 6/1998 | Gage et al. |
| 5,853,385 A | 12/1998 | Emerich et al. |
| 5,869,463 A | 2/1999 | Major et al. |
| 5,871,767 A | 2/1999 | Dionne et al. |
| 5,888,705 A | 3/1999 | Rubin et al. .............. 435/366 |
| 5,898,066 A | 4/1999 | Benowitz et al. |
| 5,968,829 A | 10/1999 | Carpenter |
| 6,001,647 A | 12/1999 | Peck et al. |
| 6,090,400 A * | 7/2000 | Elliott .................. 424/422 |
| 6,146,653 A * | 11/2000 | Elliott .................. 424/422 |
| 6,225,310 B1 * | 5/2001 | Nielsen et al. .......... 514/222.8 |
| 6,365,385 B1 | 4/2002 | Opara |
| 6,432,710 B1 * | 8/2002 | Boss et al. ............... 435/366 |
| 6,716,246 B1 | 4/2004 | Gonzalez |
| 2003/0044391 A1 | 3/2003 | Elliott et al |
| 2004/0014212 A1 | 1/2004 | Elliott et al. |
| 2004/0033216 A1 | 2/2004 | Elliott et al. |
| 2004/0213768 A1 | 10/2004 | Elliott et al. |
| 2005/0042746 A1 | 2/2005 | Garkavenko |
| 2005/0106128 A1 | 5/2005 | Elliott et al. |

FOREIGN PATENT DOCUMENTS

| AU | 22893/95 | 11/1995 |
| AU | 81864/98 | 3/1999 |
| AU | 29135/99 | 10/1999 |
| CA | 2187803 | 10/1995 |
| CA | 2216055 | 3/1999 |
| EP | 0559307 A1 | 9/1993 |
| EP | 0755258 B1 | 1/2002 |
| GB | 2 369 828 A | 6/2002 |
| NZ | 250834 B | 5/1997 |
| NZ | 502473 | 1/2000 |
| NZ | 337792 | 9/2000 |

(Continued)

OTHER PUBLICATIONS

Rayat et al, Diabetes 1998;47:1406-11.*

(Continued)

*Primary Examiner*—Q. Janice Li
(74) *Attorney, Agent, or Firm*—Haynes and Boone LLP; Mark D. Moore

(57) ABSTRACT

The invention relates to developments in the treatment of diabetes in mammals. Particularly it relates to a method of preparing a xenotransplantable porcine islet preparation capable upon xenotransplantation of producing porcine insulin in an appropriate recipient mammal, the method including or comprising the steps of:

(I) harvesting the pancreas of piglets at or near full term gestation, and
(ii) extracting pancreatic β islet cells from the harvested pancreas wherein the islets (at least at some stage in the performance of the method) are exposed to nicotinamide.

Further, the invention relates to a method of encapsulation of a xenotransplantable porcine islet preparation, and transplantation of such a preparation, or a capsule containing such a preparation, into an appropriate recipient mammal.

17 Claims, 4 Drawing Sheets

FOREIGN PATENT DOCUMENTS

| | | |
|---|---|---|
| NZ | 507616 | 10/2000 |
| NZ | 515310 | 11/2001 |
| WO | WO95/28167 | 10/1995 |
| WO | WO 96/40178 | 12/1996 |
| WO | WO97/07668 | 3/1997 |
| WO | WO99/36565 | 7/1999 |
| WO | WO99/46982 | 9/1999 |
| WO | WO99/49734 | 10/1999 |
| WO | WO99/56770 | 11/1999 |
| WO | WO00/66188 A2 | 11/2000 |
| WO | WO00/66188 A3 | 11/2000 |
| WO | WO01/19182 A1 | 3/2001 |
| WO | WO01/52871 A1 | 7/2001 |
| WO | WO02/32437 A1 | 4/2002 |
| WO | WO03/027270 A1 | 4/2003 |
| WO | WO03/039566 A2 | 5/2003 |
| WO | WO03/039566 A3 | 5/2003 |

OTHER PUBLICATIONS

Clark et al, Endocrinol 1990;126:1895-1903.*
Saura et al, Neuroendocrinol Jan. 18, 1999;161-4.*
Pu et al, Brit J Pharmacol 1996;118:1072-8.*
Kallmann et al, Life Sciences 1992;51;671-8.*
Elliott et al, Ann N Y Acad Sci. Nov. 30, 1993;696:333-41.*
Ngo, in The Protein Folding Problem and Tertiary Structure Prediction, Merz et al. (eds.), Birkhauser Boston: Boston, MA, 1994.*
Rudinger, in Peptide Hormones, Parsons (ed.), University Park Press: Baltimore, MD, pp. 1-7, 1976.*
Sun "Porcine Pancreatic Islets: Isolation, Microencapsulation and Xenotransplantation", Artificial Organs, 727-33 1993.
Maki "Porcine islet xenotransplantation utilizing a vascularized bioartificial pancreas" Annals of Transplantation, 69-71, 1997.
Lanza Biohybrid Artificial Pancreas: long-Term Function of Discordant Islet Xenografts in Streptozotocin Diabetic Rats, Transplantation, 1067-1072, 1993.
Sun et al "Normalisation of Diabetes in Spontaneously Diabetic Cynomologus Monkeys by Xenografts of Microencapsulated Porcine Islets without Immunosuppression" Journal of Clinical Investigation 1417-22 '96.
Calafiore, Riccardo. "Actual Perspectives in Biohybrid Artificial Pancreas for the Therapy of Type I, Insulin-Dependent Diabetes Mellitus" *Diabetes/Metabolism Reviews*. vol. 14, No. 4, Dec. 1998, pp. 315-324.
Brandhorst, Heide, et al. "Significant Progress in Porcine Islet Mass Isolation Utilizing Liberase HI for Enzymatic Low Temperature Pancreas Digestion" *Transplantation*. vol. 68, No. 3, Aug. 15, 1999, pp. 355-361.
Cavanagh, T.J., et al. "Improved Pig Islet Yield and Post-Culture Recovery Using Liberase PI Purified Enzyme Blend" *Transplantation Proceedings*. vol. 30, No. 2, Mar. 1998, p. 367.
Basta, G., et al. "Xenotransplantation of Microencapsulated Neonatal Porcine Islets (NIP) in Diabetic Recipients: Pre-clinical Trials" *ACTA Diabetologica*. vol. 37, No. 3, Sep. 2000, p. 145.
Barnes et al., "Influence of Recipient Oocyte Cell Cycle Stage on DNA Synthesis, Nuclear Envelope Breakdown, Chromosome Constitution and Development in Nuclear Transplant Bovine Embryos," *Mol. Reprod. Dev.*, 36:33-41, 1993.
Beal et al., "Differential Sparing of Somatostatin-Neuropeptide Y and Cholinergic Neurons following Striatal Excitotoxin Lesions," *Synapse*, 3(1):38-47, 1989.
Beattie et al., "Regulation of Proliferation and Differentiation of Human Fetal Pancreatic Islet Cells by Extracellular Matrix. Hepatocyte Growth Factor, and Cell-Cell Contact," *Diabetes*, 45:1223-1228, 1996.
Boquest et al., "Flow Cytometric Cell Cycle Analysis of Cultured Porcine Fetal Fibroblast Cells," *Biol. Reprod.*, 60:1013-1019, 1999.
Borlongan et al. "Locomotor and Passive Avoidance Deficits Following Occlusion of the Middle Cerebral Artery," *Physiology & Behavior*, 58:909-17, 1995.

Borlongan et al., "Elevated Body Swing Test: A New Behavioral Parameter for Rats with 6-Hydroxydopamine-Induced Hemiparkinsonism," *Neurosci.*, 15:5372-8, 1995.
Borlongan et al., "Striatal Dopamine-Mediated Motor Behavior is Altered Following Occlusion of the Middle Cerebral Artery," *Pharmacology Biochemistry and Behavior*, 52:225-9, 1995.
Borlongan et al. "Intercerebral Transplantation of Porcine Choroids Plexus Structural and Functional Neuroprotection in a Rodent Model of Stroke," *Stroke*, 35(9):2206-10, 2004.
Calafiore et al., "Effects of Alginate/Polyaminoacidic Coherent Microcapsule Transplantation in Adult Pigs," *Transplant. Proc.*, 4:2126-2167, 1997.
Calafiore et al., "Vascular Graft of Microencapsulated Human Pancreatic Islets in Non-Immunosuppressed Diabetic Recipients: Preliminary results," *Diab. Nutr. Metab.*, 4:45-48, 1991.
Calafiore et al., "Transplantation of Pancreatic Islets Contained in Minimal Volume Microcapsules in Diabetic High Mammalian," *Ann. N.Y. Acad. Sci.*, 875:219-232, 1999.
Campbell et al., "Cell Cycle Co-Ordination in Embryo Cloning by Nuclear Transfer," *Reviews Repro.*, 1:40-46, 1996.
Campbell et al., "Sheep Cloned by Nuclear Transfer From a Cultured Cell Line," *Nature*, 380:64-66, 1996.
Campbell et al., "Production of Live Lambs Following Nuclear Transfer of Cultured Embryonic Disc Cells," *Theriogenology*, 43:153-365; Abstract No. 181, 1995.
Campbell et al., "Improved Development of Blastocyst of Ovine Nuclear Transfer Embryos Reconstructed During the Presumptive S-phase of Enucleated Activated Oocytes," *Biol. Reprod.*, 50:1385-1394, 1994.
Campbell et al., "Nuclear-Cytoplasmic Interactions During the First Cell Cycle of Nuclear Transfer Reconstructed Bovine Embryos: Implications for Deoxyribonucleic Acid Replication and Development," *Biol. Reprod.*, 49:933-942, 1993.
Cheng, "Cationic Lipid Formulations for Intracellular Gene Delivery of Cystic Fibrosis Transmembrane Conductance Rugulator to Airway Epithelia," *Methods in Enzymology*, 292:697-717, 1998.
Cibelli et al., "Cloned Transgenic Calves Produced From Neoquiescent Fetal Fibroblast," *Science*, 280:1256-1258, 1998.
Collas et al., "Influence of Cell Cycle Stage of the Donor Nucleus on Development of Nuclear Transplant Rabbit Embryos," *Biol. Reprod.*, 46:492-500, 1992.
Collas et al., "Effect of Donor Cell Cycle Stage on Chromatin and Spindle Morphology in Nuclear Transplant Rabbit Embryos," *Biol. Reprod.*, 46:501-511, 1992.
Czolowska et al., "Behaviour of Thymocyte Nuclei in Non-Activated and Activated Mouse Oocytes," *J. Cell Sci.*, 69:19-34, 1984.
Elliott et al., "No Evidence of Infection With Porcine Endogenous Retrovirus in Recipients of Encapsulated Porcine Islet Xenografts," *Cell Transplantation*, 9:895-901, 2000.
Emerich et al., "Implants of Encapsulated Human CNTF-Producing Fibroblasts Prevent Behavioral Deficits and Striatal Degeneration in a Rodent Model of Huntington's Disease," *J. Neurosci.*, 16(16):5168-5181, 1996.
Fahn et al., "Double Blind Controlled Trial of Human Embryonic Dopaminergic Tissue Transplants in Advanced Parkinson's Disease: Clinical Outcomes," *Neurology*, 52 [Suppl 2]:A405, Apr. 1999.
Flotte et al., "Gene Therapy in Cystic Fibrosis," *Chest;* 120(3):1245-1315, 2001.
Fukuda et al., "Astrocytes Are More Vulnerable Than Neurons to Cellular $Ca^{2+}$ Overload Induced By A Mitochondrial Toxin, 3-Nitropropionic Acid," *Neurosci.*, 87(2):497-507, 1998.
Gadbois et al., "Multiple Kinase Arrest Points in the G1 Phase of Nontransformed Mammalian Cells are Absent in Transformed Cells," *Proc. Natl. Acad. Sci.*, 89:8626-8630, 1992.
Gardner et al., "Enhanced Rates of Cleavage and Development for Sheet Zygotes Cultured to the Blastocyst Stage in Vitro in the Absence of Serum and Somatic Cells: Amino Acids, Vitamins and Culturing Embryos in Groups Stimulate Development," *Biol. Reprod.*, 50:390-400, 1994.
Kitada Masaaki et al. "Axonal Regeneration in the Central Nervous System is Enhanced by Ependymal Cell Transplants," *Neosci. Research Supplement*, 22:S318, 1998. XP000960785 21st Annual Meeting of the Japan Neuroscience Society and the First Joint Meeting of the Japan Neuroscience Society and the Japanese Society for Neurochemistry; Tokyo, Japan; Sep. 21-23, 1998. ISSN: 0921-8696.

Kopyov et al., "Safety of Intrastriatal Neurotransplantation for Huntington's Disease Patients," *Experimental Neurology,* 149:97-108, 1998.

Korbutt et al, "Cotransplantation of Allogeneic Islets with Allogeneic Testicular Cell Aggregates Allows Long-Term Graft Survival Without Systemic Immunosuppression," *Diabetes,* 46:317-322, Feb. 1997.

Kordower et al., "Cellular Delivery of Trophic Factors for the Treatment of Huntington's Disease: Is Neuroprotection Possible?," *Experimental Neurology,* 159:4-20, 1999.

Korsgren et al., "Functional and Morphological Differentiation of Fetal Porcine Islet-Like Cell Clusters After Transplantation into Nude Mice," *Diabetologia,* 34:379-386, 1991.

Krewson et al, "Distribution of Nerve Growth Factor Following Direct Delivery to Brain Interstitium," *Brain Res.,* 680 (1-2):196-206, 1995.

Lindvall, et al, "Histochemical, Ultrastructural and Functional Evidence for a Neurogenic Control of Cerebrospinal Fluid Production From the Choroid Plexus," *Acta Physiologica Scand. Suppl.,* 452:77-86, 1977.

London et al., "A Simple Method for the Release of Islets by Controlled Collagenase Digestion of the Human Pancreas," *Transplantation,* 49(6):1109-1113, Jun. 1990.

Luca et al., "Sertoli Cell-Induced Reversal of Audit Rat Pancreatic Islet B-Cells into Fetal-Like Status: Potential Implications for Islet Transplantation into Type 1 Diabetes Mellitus," *J. Invest. Medicine,* 48(6):441-448, Nov. 2000.

Luca, et al., "Mitogenic Effects of Rat Sertoli Cells on Adult Homologous Islet B-Cells: In Vitro and In Vivo Studies," *Transplant. Proc.,* 33:681-382, 2001.

Maria-Engler S.S. et al., "Microencapsulation and Tissue Engineering as an Alternative Treatment of Diabetes," *Braz. J. Med. Biol. Res.,* 34(6):691-697, 2001.

Marti et al., "Systemic Hypoxia Changes the Organ-Specific Distribution of Vascular Endothelial Growth Factor and its Receptors," *Proc. Natl. Acad. Sci.,* 95:15809-15814, 1998.

Mehler et al., "Progenitor Cell Biology Implications for Neural Regeneration," *Arch. Nerol,* 56:780-784, 1999.

Orive et al, "Cell Encapsulation: Promise and Progress," *Nature Medicine,* 9(1):104-107, 2003.

Otaegui et al., "Transfer of Nuclei From 8-Cell Stage Mouse Embryos Following Use of Nocodazole to Control the Cell Cycle," *Mol. Reprod. Dev.,* 39:147-52, 1994.

Pardridge, "Peptide Drug Delivery To The Brain," 1991, 114-122; 305; 307, New York: Raven Press.

Paxinos et al., "The Rat Brain in Sterotaxic Coordinates," *Acadmeic Press,* New York, 1986.

Pedersen, "Embryonic Stem Cells for Medicine," *Scientific American,* 44-49, Apr. 1999.

Perry et al., "Mammalian Transgenesis by Intracytoplasmic Sperm Injection," *Science,* 284:1180-1183, 1999.

Pinto-Correia et al., "Factors Involved in Nuclear Reprogramming During Early Development in the Rabbit," *Mol. Reprod. Dev.,* 40:292-304, 1995.

Rabinovitch et al., "Factors From Fibroblast Promote Pancreatic Islet B Cell Survival in Tissue Culture," *Diabetes,* 28:1108-1113, 1979.

Ramiya et al. "Reversal of Insulin-Dependant Diabetes Using Islets Generated In Vitro from Pancreatic Stems Cells," *Nature Medicine,* 6(3):278-282, 2000.

Rao et al, "Choroid Plexus Epithelial Expresion of *MDR1* P Glycoprotein And Multidrug Resistance-Associated Protein Contribute to the Blood-Cerebrospinal-Fluid Drug-Permeability Barrier," *Proc. Natl. Acad. Sci.,* 96:3900-3905, 1999.

Rayat et al., "Potential Application of Neonatal Porcine Islets as Treatment for Type 1 Diabetes: A Review," *Ann. N.Y. Acad. Sci.,* 875:175-188, 1999.

Ricordi, "Chapter 10: The Automated Method for Islet Transportation", Pancreatic Islet Cell Transportation: 1892-1992, one century of transplantation for diabetes, R.G. Landes Publisher, Austin, pp. 99-112, 1992.

Rubin, "Emerging Therapies for Cystic Fibrosis Lung Disease," *Chest,* 115:1120-1126, 1999.

Sakamoto et al., "Improvement of Porcine Islet Culture with Porcine Serum," *Acta Diabetologica,* 34:128, 1997.

Salzberg-Brenhouse et al., "Inhibitors of Cyclooxygenase-2, but Not Cyclooxygenase-1 Provide Structural and Functional Protection against Quinolinic Acid-Induced Neurodegeneration," *J. Pharmacology and Experimental Therapeutics,* 306:218-228, 2003.

Schnieke et al., "Human Factor IX Transgenic Sheep Produced by Transfer of Nuclei From Transfected Fetal Fibroblasts," *Science,* 278:2130-2133, 1997.

Segal, "The Choriod Plexuses and the Barriers Between the Blood and the Cerebrospinal Fluid," *Cell Mol. Neurobio.,* 20(2):183-196, 2000.

Selawry et al., "Sertoli Cell-Enriched Fractions in Successful Islet Cell Transplantation," *Cell Transplantation,* 2:123-129, 1993.

Selawry et al., "Sertoli Cell-Induced Effects on Functional and Structural Characteristics of Isolated Neonatal Porcine Islets," *Cell Transplantation,* 5(5):517-524, 1996.

Shapiro et al., "Islet Transportation in Seven Patients with Type 1 Diabetes Mellitus Using a Glucocorticoid-Free Immunosuppressive Regimen," *The New England J of Medicine,* 343:230-238, 2000.

Shapiro et al., "Pancreatic Islet Transplantation in the Treatment of Diabetes Mellitus," *Best Pract. Res. Clin. Endocrin. Metab.,* 15:241-264, 2001.

Sherwood et al., "Defining Cellular Senescence in IMR-90 Cells: A Flow Cytometric Analysis," *Proc. Natl. Acad. Sci.* 85:9086-9090, 1988.

Stice et al., "Pluripotent Bovine Embryonic Cell Lines Direct Embryonic Development Following Nuclear Transfer," *Biol. Reprod.,* 54:100-110, 1996.

Suarez-Pinzon et al, "Testicular Sertoli Cells Protect Islet B-Cells From Autoimmune Destruction in NOD Mice by a Transforming Growth Factor B1-Dependent Mechanism," *Diabetes,* 49:1810-1818, 2000.

Susko-Parrish et al., "Inhibition of Protein Kinases After an Induced Calcium Transient Causes Transition of Bovine Oocytes to Embryonic Cycles Without Meiotic Completion," *Develop. Biol.,* 166:729-739, 1994.

Tada et al., "Embryonic Germ Cells Induce Epigenetic Reprogramming of Somatic Nucleus in Hybrid Cells," *EMBO J.,* 16:6510-6520, 1997.

Thompson et al., "Effect of Oxygen Concentration on In Vitro Development of Preimplantation Oheep and Cattle Embryos," *J. Reprod. Fert.,* 89:573-578, 1990.

Thomson et al., "Embryonic Stem Cell Lines Derived From Human Blastocysts," *Science,* 282:1145-1147, 1998.

Tonelli et al., "New and Emerging Therapies for Pulmonary Complications of Cystic Fibrosis," *Drugs 2001,* 61(10):1379-1385, 2001.

Verhoeven et al., "Influence of Coculture with Sertoli Cells on Steroidogenesis in Immature Rat Leydig Cells," *Molecular Cellular Endocrinology,* 71:239-251, 1990.

Vignon et al., "Development of Bovine Nuclear Transfer Embryos Reconstituted With Quiescent and Proliferative Skin Fibroblasts," *Theriogenology,* 51:161-438; Abstract No. 216, 1999.

Vignon et al., "Developmental Potential of Bovine Embryos Reconstructed From Enucleated Matured Oocytes Fused With Cultured Somatic Cells," *C R Acad. Sci. Paris,* 321:735-745, 1998.

Wakayama et al., "Mice Cloned From Embryonic Stem Cells," *Proc. Natl. Acad. Sci.,* 96(26):14984-14989, 1999.

Wakayama et al., "Cloning of Male Mice From Adult Tail-Tip Cells," *Nature Genetics,* 22:127-128, 1999.

Wall et al., "Transgenic Dairy Cattle: Genetic Engineering on a Large Scale," *J. Dairy Science,* 80:2213-2224, 1997.

Walter et al., "Distinct Sites of Insulin-Like Growth Factor (IGF)-II Expression and Localization in Lesioned Rat Brain: Possible Roles of IGF Binding Proteins (IGFBPs) in the Mediation of IGF-II Activity," *Endocrinology,* 140(I) 520-532, 1999.

Wang et al., "Protective Effects of Glial Cells Line-Derived Neurotrphic Factor in Ischemic Brain Injury," *Ann. N.Y. Acad. Sci.,* 962: 423-437, 2002.

Weber et al., "Evaluation of Graft-Host Response for Various Tissue Sources and Animal Models," *Ann. N.Y. Acad. Sci.,* 875:233-254, 1999.

Wells et al., "Adult Somatic Cell Nuclear Transfer is Used to Preserve the Last Surviving Cow of the Enderby Island Cattle Breed," *Reprod. Fertil. Dev.,* 10:369-378, 1999.

Wells et al., "Production of Cloned Bovine Fetuses Following Nuclear Transfer With Cells From a Fetal Fibroblast Cell Line," *Theriogenology,* 49:153-404; Abstract No. 330, 1998.

Weiss, "Xenografts and Retroviruses," *Science,* 285:1221-1222, 1999.

Wilmut et al., "Viable Offspring Derived From Fetal and Adult Mammalian Cells," *Nature,* 385:810-813, 1997.

Zakhartchenko et al., "Effects of Serum Starvation and Re-Cloning on the Efficiency of Nuclear Transfer Using Bovine Fetal Fibroblasts," *J. Reprod. Fertil,* 115:325-331, 1999.

Zhang et al, "Migration and Differentiation of Adult Rat Subventricular Zone Progenitor Cells Transplanted into the Adule Rat Striatum," *Neuroscience,* 116:373-382, 2003.

Examination Report to Australian Application No. 74624/00; Sep. 21, 2004.

Examination Report to Australian Application No. 74624/00; Nov. 18, 2004.

Examination Report to Australian Application No. 74624/00; Mar. 16, 2005.

Examination Report to Australian Application No. 74624/00; Apr. 23, 2005.

Examination Report to Australian Application No. 2002211122, Jun. 10, 2005.

Examination Report to EP Application No. 00 925 757.7; Oct. 29, 2003.

Examination Report to EP Application No. 01 942 558.6; Feb. 24, 2004.

Examination Report to Great Britain Application No. GB0205915.2; Sep. 24, 2003.

Examination Report to Great Britain Application No. GB0205915.2; Apr. 26, 2004.

Examination Report to Great Britain Application No. GB0205915.2; Aug. 11, 2004.

Examination Report to Great Britain Application No. GB0205915.2; Sep. 22, 2004.

Examination Report to Great Britain Application No. GB0205915.2; Oct. 13, 2004.

Examination Report to Great Britain Application No. GB0205915.2;Oct. 15, 2004.

Examination Report to New Zealand Application No. 337792; Sep. 20, 2000.

Examination Report to New Zealand Application No. 531956; Jun. 13, 2005.

International Examination Report, Application No. PCT/NZ00/00179; Jan. 17, 2002.

International Examination Report, Application No. PCT/NZ01/00228; Dec. 16, 2002.

International Search Report Application No. PCT/AU99/00165; Apr. 16, 1999.

International Search Report, Application No. PCT/NZ00/00064; Nov. 28, 2000.

International Search Report, Application No. PCT/NZ00/00179; Nov. 10, 2000.

International Search Report, Application No. PCT/NZ01/00006; Apr. 26, 2001.

International Search Report, Application No. PCT/NZ01/00228; Mar. 11, 2002.

International Search Report, Application No. PCT/NZ02/00197; Nov. 28, 2002.

International Search Report, Application No. PCT/NZ02/00235; Feb. 21, 2003.

Written Opinion to Application No. PCT/NZ00/00179, Dec. 13, 2001.

Written Opinion to Application No. PCT/NZ00/00179, Oct. 18, 2001.

Written Opinion to Application No. PCT/NZ00/00179, Aug. 3, 2001.

Written Opinion to Application No. PCT/NZ00/00179, Mar. 27, 2001.

* cited by examiner

PREPARATION AND XENOTRANSPLANTATION OF PORCINE ISLETS

INTRODUCTION

The present invention relates to improvements in and/or relating to the treatment of diabetes using xenotransplantation. More particularly but not exclusively the present invention relates to the preparation of viable xenotransplantable porcine islets and/or the treatment of a mammalian patient (including humans) suffering from diabetes involving the transplantation into the mammal of viable porcine islets capable of producing insulin within the host.

BACKGROUND

Type 1 (insulin-dependent) diabetes mellitus is a common endocrine disorder that results in substantial morbidity and mortality, and leads to considerable financial costs to individual patients and healthcare systems.

Treatment with insulin, while life-saving, often does not provide sufficient control of blood glucose to prevent the feared complications of the disease, which has provided the impetus for intensive research into better methods of sustaining normoglycaemia.

Among the newer treatment strategies that have been proposed, transplantation of pancreatic β islet cells, obtained either from other humans or animals, has received the most attention worldwide. This is because transplantation can restore not only the insulin-secreting unit, but also the precise fine tuning of insulin release in response to multiple neural and humoral signals arising within and beyond the islets of Langerhans.

Human islet cell transplantation is limited by the shortage of human islet tissue. The use of pig islet cells is currently viewed as the most promising alternative since:

(a) the supply of pig cells can be readily expanded by optimising the supply of donor animals;
(b) pig and human insulin have close structural similarities; and
(c) physiological glucose levels in pigs are similar to those in humans.

The rationale for this treatment approach (termed 'xenotransplantation') is that the implanted pig islets have the potential to mimic the normal physiological insulin response in type 1 diabetics such that near-normal blood glucose levels may be achievable without insulin administration or with a reduced requirement for it. As a consequence, long-term diabetes complications may be prevented and patients should experience less hypoglycaemia than they do with the currently recommended 'intensive' insulin regimens.

OBJECT

It is an object of the present invention to provide a method of preparing porcine islets which produces islets viable for xenotransplantation into a mammalian patient the islets being capable of producing insulin within a mammalian host, as well as the islet preparation so produced, or irrespectively or how produced, or a similar form.

Alternatively or additionally, it is a further object to provide a method of treating a mammalian patient suffering from diabetes which involves the xenotransplantation of porcine islets into the mammalian patient.

Alternatively or additionally, it is a further object to at least provide the public or medical community with a useful alternative approach to diabetes treatment.

STATEMENTS OF INVENTION

In a first aspect the invention consists in a method of preparing a xenotransplantable porcine islet preparation capable upon xenotransplantation of producing porcine insulin in an appropriate recipient mammal, the method including or comprising the steps of:

(I) harvesting the pancreas of piglets at or near fall term gestation, and
(ii) extracting pancreatic β islet cells from the harvested pancreas wherein the islets (at least at some stage in the performance of the method) are exposed to nicotinamide.

Preferably the method includes or comprises the steps of:

(I) harvesting the pancreas of piglets at or near full term gestation, and
(ii) preparing a culture of the pancreatic β islet cells
(iii) simultaneously with step (ii) and/or after step (ii) extracting pancreatic β islet cells from the culture of the harvested pancreas Preferably said piglets from which the pancreatic β islet cells are extracted are at from −20 to +10 days full term gestation.

Preferably said piglets are at from −7 to +10 days full term gestation.

Preferably the extraction is performed using a suitable collagenase

Preferably the collagenase is selected from human Liberase® or porcine Liberase®.

Preferably said collagenase is human Liberase®.

Preferably the culture includes harvested pancreas in a supportive mammalian albumin substantially free of non-human microbiological agents.

Preferably the mammalian albumin is human serum albumin (HSA).

Preferably the islets are treated with nicotinamide after their extraction from the pancreas.

Preferably the method includes the further step of treating the islets with IgF-1 or the N-terminal tripeptide of IgF-1 (GPE).

Preferably the exposure to $IgF_1$ or to GPE is greater for those cells from piglets furthest from full term gestation, more preferably there is exposure to $IgF_1$ for all cells extracted irrespective of their relationship to full term gestation.

Preferably the pancreas and/or islets are subject to a trauma protecting agent selected from suitable anaesthetic agents.

Preferably the trauma protecting agent is lignocaine.

Preferably step (iii) of the method includes mechanically reducing the harvested pancreas in the presence of the islet trauma protecting agent.

Preferably an antibiotic is associated with the islet cells.

Preferably said antibiotic is ciproxin.

In another aspect the invention consists in a method of preparing a xenotransplantable porcine islet preparation capable upon xenotransplantation of producing porcine insulin in an appropriate recipient mammal, said method including or comprising the steps of:

(I) harvesting the pancreas of piglets at or near full term gestation, and
(ii) preparing a culture of the pancreatic β islet cells (iii) simultaneously with step (ii) and/or after step (ii) extracting pancreatic β islet cells from the culture of the harvested pancreas and (iv) encapsulating the islet cells with a biocompatible xenotransplantable material, said material in vivo being both glucose and insulin porous, wherein nicotinamide is introduced to the islets or islet cells prior to encapsulation at any one or more stages of the procedure.

Preferably said piglets at or near full term gestation from which the pancreatic β islet cells are extracted are at from −20 to +10 days full term gestation.

Preferably said piglets are at from −7 to +10 days full term gestation.

Preferably the extraction is performed using a suitable collagenase.

Preferably the collagenase is selected from human Liberase® or porcine Liberase®.

Preferably said collagenase is human Liberase®.

Preferably the culture includes harvested pancreas in a supportive mammalian albumin substantially free of non-human microbiological agents.

Preferably the mammalian albumin is human serum albumin (HSA).

Preferably the islets are treated with nicotinamide after their extraction from the pancreas.

Preferably the method includes the further step of treating the islets with IgF-1 or the N-terminal tripeptide of IgF-1 (GPE).

Preferably the exposure to $IgF_1$ or to GPE is greater for those cells from piglets furthest from full term gestation but preferably there is exposure to $IgF_1$ for all cells extracted irrespective of their relationship to full term gestation.

Preferably the pancreas and/or islets are subject to a trauma protecting agent selected from suitable anaesthetic agents.

Preferably the trauma protecting agent is lignocaine.

Preferably step (iii) of the method includes mechanically reducing the harvested pancreas in the presence of the islet trauma protecting agent.

Preferably an antibiotic is associated with the islet cells.

Preferably said antibiotic is ciproxin.

Preferably said biocompatible material is a suitable alginate.

Preferably the alginate is in ultra pure form.

Preferably each islet or grouping of islets is entrapped in an in vivo insulin and glucose porous biocompatible alginate or alginate-like surround.

Preferably the encapsulation provides a surround which prevents, once implanted, direct tissue contact with the islets.

Preferably each encapsulation involves presenting islets and a suitable alginate solution into a source of compatible cations thereby to entrap the islets in a cation—alginate gel.

Preferably said cation alginate gel is calcium-alginate gel.

Preferably said alginate used in the solution is sodium alginate, and the islet and sodium alginate solution is presented as a droplet into a bath of suitable cations.

Preferably the islet and sodium alginate solution is of 1.6% w/w.

Preferably the islet and sodium alginate solution is presented as a droplet through a droplet generating needle.

Preferably the suitable cations are calcium chloride.

Preferably the gel encased islets are coated with a positively charged material and thereafter are provided with an outer coat of a suitable alginate.

Preferably the positive charging material is poly-L-ornithine.

Preferably the gel entrapping the islets within the outer coating is then liquified.

Preferably the liquification involves or comes about by the addition of sodium citrate.

Preferably the encapsulation produces capsules.

Preferably the capsules contain a plurality of islet cells.

Preferably the capsules contain substantially three islet cells.

Preferably the capsules have a diameter of substantially from about 300 to 400 microns.

Preferably following liquification of the alginate entrapping the islets there are the further steps of:

washing the capsules further coating the capsules with alginate to neutralize any residual change on the poly-L-ornithine coating and prevents direct contact of the poly-L-ornithine with tissues when the entire capsule is transplanted.

Preferably the alginate has been produced via a process involving the steps of:

Seaweed harvest→Washing→Alginate extraction→Filtration →Precipitation→Drying.

In another aspect the invention is a xenotransplantable capsule prepared according to the above method.

In another aspect the present invention is a xenotransplantable preparation being or including viable porcine islets prepared according to a method of the present invention.

In still a further aspect the present invention consist in a xenotransplantable capsule of at least one porcine pancreatic β islet cell comprising at least one viable porcine pancreatic β islet cell enclosed in an in vivo glucose porous and insulin porous biocompatible material.

In another aspect the invention consists in a method for treatment of a mammalian patient suffering from diabetes which comprises:

(a) extracting pancreatic β islet cells from piglets at or near full term gestation;

(b) Simultaneously with, and/or after a), treating said islets with nicotinamide, (c) encapsulating said islets in a biocompatible material which will allow in vivo glucose movement to and insulin movement from the islets, and (d) injecting or otherwise implanting the encapsulated islet cells of step (c) so as to transplant into said mammalian patient an effective amount of viable piglet islet cells capable of producing insulin in the patient, Preferably the method further includes the step of administering nicotinamide to the mammalian patient at least subsequent to transplantation.

Preferably the method further includes the step of prescribing to the patient, prior to or after the implantation step, a casein-free diet (as herein described).

Preferably the method further includes the step of exposure of the pancreatic β islet cells at some stage after extraction from the piglets and prior to encapsulation to $IgF_1$ or to GPE.

Preferably the harvesting of the islets at least during any substantial confrontation (eg; mincing and/or enzymatic challenge) is in the present of a trauma protecting agent.

Preferably the trauma protecting agent is used during the isolation and/or preparation thereof for encapsulation.

Preferably the agent is a trauma protecting agent is selected from suitable anaesthetic agents.

Preferably the trauma protecting agent is lignocaine.

Preferably the patient prior to, during or after the step (d) has been subjected to a cholesterol lowering drug regime.

Preferably the drug is of the "statin" family.

Preferably the drug is pravastatin.

Preferably the yield of viable porcine islets obtained from the extraction of step a) is enhanced by the use of a suitable collagenase.

Preferably the collagenase is selected from human Liberase® or porcine Liberase®.

Preferably said collagenase is human Liberase®.

Preferably the extraction of step a) includes mechanical treatment of the islets.

Preferably the mechanical treatment follows application of a suitable anaesthetic to the pancreatic tissue.

Preferably the anaesthetic is lignocaine.

Preferably said piglets from which the pancreatic β islet cells are extracted are at from −20 to +10 days full term gestation.

Preferably said piglets are at from −7 to +10 days full term gestation.

Preferably said biocompatible material is a suitable alginate.

Preferably the alginate is in ultra pure form.

Preferably each islet or grouping of islets is entrapped in an in vivo insulin and glucose porous biocompatible alginate or alginate-like surround.

Preferably the encapsulation provides a surround which prevents, once implanted, direct tissue contact with the islets.

Preferably each encapsulation involves presenting islets and a suitable alginate solution into a source of compatible cations thereby to entrap the islets in a cation—alginate gel.

Preferably said cation alginate gel is calcium-alginate gel.

Preferably said alginate used in the solution is sodium alginate, and the islet and sodium alginate solution is presented as a droplet into a bath of suitable cations.

Preferably the islet and sodium alginate solution is of 1.6% w/w.

Preferably the islet and sodium alginate solution is presented as a droplet through a droplet generating needle.

Preferably the suitable cations are calcium chloride.

Preferably the gel encased islets are coated with a positively charged material and thereafter are provided with an outer coat of a suitable alginate.

Preferably the positive charging material is poly-L-ornithine.

Preferably the gel entrapping the islets within the outer coating is then liquified.

Preferably the liquification involves or comes about by the addition of sodium citrate.

Preferably the encapsulation produces capsules.

Preferably the capsules contain a plurality of islet cells.

Preferably the capsules contain substantially three islet cells.

Preferably the capsules have a diameter of substantially from about 300 to 400 microns.

Preferably following liquification of the alginate entrapping the islets there are the further steps of:
  washing the capsules
  further coating the capsules with alginate to neutralize any residual change on the poly-L-ornithine coating and prevents direct contact of the poly-L-ornithine with tissues when the entire capsule is transplanted.

Preferably the alginate has been produced via a process involving the steps of:
  Seaweed harvest→Washing→Alginate extractions→Filtration→Precipitation→Drying.

In yet another aspect the invention is a method for the treatment of a mammalian patient suffering from or predisposed to diabetes, said method including or comprising the steps of:

(A) (i) harvesting the pancreas of piglets at or near full term gestation,
  (ii) culturing the harvested pancreas in Mammalian Albumin substantially free of non-human microbiological agents,
  (iii) simultaneously with step (ii) and/or after step (ii), extracting the islets from the harvested pancreas using a suitable Liberase®,
  wherein the islets (at least at some stage in the performance of (A)) are exposed to nicotinamide;

(B) (i) encapsulating the islets prepared by (A) with a suitable encapsulation material that allows both glucose and insulin movement therethrough, and
  (ii) implanting the encapsulated porcine islets into the recipient mammal.

Preferably the Liberase® is selected from human Liberase® or porcine Liberase®.

Preferably the Liberase is human Liberase®.

Preferably the extraction of step a) includes mechanical treatment of the islets.

Preferably the mechanical treatment follows application of a suitable anaesthetic to the pancreatic tissue.

Preferably the anaesthetic is lignocaine.

Preferably the method further includes the step of administering nicotinamide to the recipient mammal prior to or after the implantation step.

Preferably the method further includes the step of prescribing for the patient, prior to or after the implantation step, a casein-free diet (as described herein).

Preferably the method further includes the step of subjecting the patient prior to or after the implantation step to a cholesterol lower drug regime.

Preferably the cholesterol lowering drug is of the "statin" family

Preferably said cholesterol lowering drug is pravastatin or simvistatin.

In a further aspect the present invention consists in encapsulated pancreatic islets of a kind useful in a method aforesaid.

In still a further aspect the present invention consists in a method of porcine β islet cell production and/or method of xenotransplantation thereof in an encapsulated form when preformed by a procedure substantially as hereinbefore described and/or substantially as hereinafter described and/or as shown in FIG. 1 of the accompanying drawings.

In a further aspect the present invention consists in any isolated porcine islets or xenotransplantable preparations including viable porcine islets where the digestion has been in accordance with the method in accordance with the present invention.

In yet another aspect the invention is a method of treating a mammalian patient predisposed to or suffering from diabetes which involves the xenotransplantation into such patient at least one capsule of the present invention.

DETAILED DISCUSSION

1. General

The present invention recognises the ability to source appropriate islets from piglets which have similar structural similarities of insulin to humans, and similar physiological glucose levels to humans. The piglets used are at or near full term gestation. The islets are converted into an appropriate xenotransplantable source of islets with viability in a human being by following certain procedures in respect of the harvesting and extraction of the islets, the treatment of the islets prior to xenotransplantation as well as regimes of use of such islets.

The major advantage of porcine islet cell transplantation over human islet cell transplantation is that the islet cell source can be readily expanded, and the biosafety of the cells can be thoroughly explored prior to transplantation. From a practical viewpoint, pancreas removal and islet cell isolation can be performed expeditiously in an ideal environment.

Important considerations relevant to the use of porcine islet cells in transplantation approaches for type 1 diabetes include the following:

The structural and biological similarities of porcine and human insulin

The fact that porcine insulin has been used to treat diabetes for several decades (and has only been replaced by human sequence insulin relatively recently); and The similarity of physiological glucose levels in pigs and humans. (Weir & Bonner-Weir 1997). This effectively means that pig islet cells can be expected to react similarly to their human counterparts in maintaining equivalent blood glucose concentrations.

2. The Nature of the Disease Causing Diabetes

Successful long-term allotransplantation of human islets can be achieved in over 80% of patients when the disease is caused by non-immune processes. In contrast, even islets obtained from a non-diabetic twin cannot reverse autoimmune diabetes long-term in the diabetic twin member. This emphasises the critical role of autoimmunuity in the failure of islet transplantation. This observation has been validated in allotransplantation of rodents with diabetes caused by autoimmunity as compared with diabetes due to pancreatectomy or chemical β cell destruction. No large animal model of autoimmune diabetes exists. It is possible that the use of islets from different species (xenotransplantation) could avoid autoimmune destruction of transplanted islets, as the immune process of xenotransplant rejection is different to that of allotransplant rejection, but this is entirely hypothetical in humans.

3. Isolation and Preparation of Porcine Islet Cells for Xenotransplantation

3a. Animal Source and Transportation

All animals intended as a source of pancreatic tissue for xenotransplantation are obtained from a specific pathogen-free (SPF) pig breeding facility which is maintained in accordance with the American Association for Accreditation of Laboratory Animal Care (AAALAC). The facility maintains a high-health status colony with excellent standards of husbandry, and operates a record system that is readily accessible and archived indefinitely. Donor sows and sires are selected with the underlying objective of producing strong heterosis in donor litters.

3b. Isolation and Purification of Islet Cells

Following surgical removal, the donor pancreases are transferred to a cleanroom facility for further processing in a cold plastic container in 50 ml tubes containing cold Hanks' Balanced Salt Solution (HBSS) with 0.2% human serum albumin (HSA) added. Blood samples from each donor are sent for virology testing and toxoplasma serology. Samples from each organ are kept in a freezer at −80° C. for future testing if necessary.

3c. Digestion

The islet cells are isolated by standard collagenase digestion of the minced pancreas via the procedure documented by Ricordi et al. (1990), though with some modifications. Using aseptic technique, the glands are distended with Liberase® (1.5 mg/ml), trimmed of excess fat, blood vessels and connective tissue, minced, and digested at 37° C. in a shaking water bath for 15 minutes at 120 rpm. The digestion is achieved using lignocaine mixed with the Liberase® solution to avoid cell damage during digestion. Following the digestion process, the cells are passed through a sterile 400 mm mesh into a sterile beaker. A second digestion process is used for any undigested tissue.

We have determined that much greater yields per neonatal pig pancreas can be obtained using either pig or human Liberase™ (eg; sourced in New Zealand from Roche) rather than collagenase. Whilst there is disclosure in "*Improved Pig Islet Yield and Post-Culture Recovery Using Liberase P1 Purified Enzyme Blend*", T J Cavanagh et al. Transplantation Proceedings 30, 367 (1998) and in "*Significant Progress In Porcine Islets Mass Isolation Utilizing Liberase® HI For Enzymatic Low-Temperature Pancreas Digestion*", H. Brandhorst et al. Transplantation Vol 68, 355–361 No. 3, Aug. 15, 1999 the yields therefore therein are low compared to those we have discovered. If, for example, in following the procedure of Brandhorst et al. there is a yield increase of islets over collagenase of from 400 to say 800 with the procedure using human Liberase® (ie; Liberase® HI) as in the Brandhorst et al. procedure but confined to neonatal porcine islets such as those as 7 days post delivery extra ordinarily larger yields are possible, namely, the equivalent to from 400 which would be the case with crude collagenase to 30000 which as can be seen as very much greater than that to be expected from following the procedure of Brandhorst et al. with pigs.

3d. Washing and Culture

The digested tissue is washed three times, and seeded into cell culture media RPMI 1640 to which is added 2% human serum albumin (HSA), 10 mmol/L nicotinamide, and antibiotic (Ciproxin).

3e. Quality Control Procedures

To exclude any contamination of the tissue, quality control procedures are undertaken on cell culture samples after isolation and before encapsulation Three days after isolation, the cell culture is tested for microbiological contamination by accredited laboratories. Testing for porcine endogenous retrovirus (PERV) is undertaken at the Virology Laboratory, Auckland Hospital.

The islet yield is determined via dithizone (DTZ) staining of the cells. Dithizone is a zinc-chelating agent and a supravital stain that selectively stains zinc in the islets of Langherhans, producing a distinctive red appearance.

The viability of the islet cells is determined using acridin orange and propidium iodide. Acridin orange is a fluorescent stain that readily passes through all cell membranes to stain the cytoplasm and nucleus. Bright green fluorescence in both the nucleus and cytoplasm on exposure to ultraviolet (UV) light denotes intact live cells. Conversely, propidium iodide is a fluorescent stain that cannot pass through an intact membrane. It emits a bright red fluorescence when exposed to UV light, and the presence of propidium iodide in a cell nucleus indicates severe damage or a dead cell.

3f. Determination of in vitro Insulin Secretory Capacity

Static glucose stimulation (SGS) is used to assess in vitro function of the porcine islets by exposing them to low and high concentrations of glucose and theophylline. Determination of the in vitro insulin secretory capacity is undertaken on both free islets (after 3 days in culture) and after their subsequent encapsulation.

4. Xenotransplantation

4a. The Viability of the Islets for Xenotransplantation

The processes by which islets are purified prior to transplantation are traumatic to these highly specialised tissues. Such trauma can induce necrosis or apoptosis—the latter can be quite delayed.

Further trauma may result from encapsulation. Processes used by us in both the preparation of islets and their encapsulation have been optimised to ensure minimal damage to the islets. Such procedures have ensured zero warm ischaemia (compared with hours with most human islet preparations), have involved the use of nicotinamide to enhance successful in vitro explantation, have involved minimal incubation time with collagenase or Liberase, have involved swift non-traumatic encapsulation technology, have involved the use of IgF-1 (or the GPE tripeptide thereof), the use of an anaesthetic such as lignocaine, and the use of an antibiotic such as ciproproxin etc.

Our preferred preparation preferably uses neonatal (7-day old) islets which is crucial in both limiting islet trauma during purification, and assuring sufficient maturation of the islets for stimulated insulin production.

The IgF-1 (Human Insulin-like Growth Factor I) is used in-order to induce unmatured porcine islets to mature to their insulin-producing form. IgF-1 is a potent mitogenic growth factor that mediates the growth promoting activities of growth hormone postnatally. Both IgF-1 and IgF-2 are expressed in many cell types and may have endocrine, autocrine and paracrine functions. The preferred form of IgF-1 we have found to be the amino-terminal tripeptide glycine-proline-glutamate of IgF-1 (GPE).

4b. Alginate Encapsulation Procedure

Sodium alginate used for this procedure is extracted from raw material sources (seaweed) and prepared in a powdered ultrapure form. The sterile sodium alginate solution (1.6%) is then utilised at the Diatranz Islet Transplant Centre to manufacture encapsulated islets.

Generally each encapsulation involves presenting islets and a suitable alginate solution (usually sodium alginate) into a source of compatible cations thereby to entrap the islets in a cation—alginate gel (usually calcium-alginate gel).

The encapsulation procedure involves extruding a mixture of islets and sodium alginate solution (1.6% w/w) through a droplet generating needle into a bath of gelling cations (calcium chloride). The islets entrapped in the calcium-alginate gel are then coated with positively charged poly-L-ornithine followed by an outer coat of alginate (0.05%). The central core of alginate is then liquefied by the addition of sodium citrate. Most capsules contain 3 islets and have a diameter of 300 to 400μm.

After liquification of the alginate entrapping the islets, the "capsules" are washed, and again coated with alginate which neutralizes any residual change on the poly-L-ornithine coating and prevents direct contact of the poly-L-ornithine with tissues when the entire capsule is transplanted.

The encapsulated islets are kept in cell culture, and then checked for contamination, insulin release and viability before transplantation. They are only released for transplantation if all quality control tests are negative.

Ideally the alginate production process has involved the following steps:

Seaweed harvest→Washing→Alginate extraction→Filtration (preferably a 0.2 μm filter→Precipitation→Drying.

The ultrapure alginate used is ideally Kelco LV produced by Monsanto-Kelco, US and has the following specifications:

1. Viscosity: 2% —100–300 cps (Brookfield 25° C., speed 3.60 rpm)
2. pH: 6.4–8.0
3. Protein content <0.5%
4. Filtration: through 0.2 μm
5. Chemical analysis:

| Ca: | <100 ppm | Mg | <40 ppm | Mn: | <10 ppm |
|---|---|---|---|---|---|
| Cu: | <40 ppm | Zn: | <40 ppm | Sr: | <40 ppm |
| Fe: | <60 ppm | Pb: | <50 ppm | As: | <100 ppb |
| Hg: | <40 ppb | Si: | <10 ppm | | |

6. Endotoxin level—measured by LAL test (at University of Perugia): 39 EU/g [NB. Any level below 100 EU/g in this test is considered endotoxin-free].
7. Molecular weight: 120,000–190,000 kD
8. Mannuronic acid (M) content: M fraction ($F_m$) 61%
9. Guluronic acid (G) content: G fraction ($F_G$) 39%

Ideally the filtration has been with a multiple filtration process employing positively charged filters that remove any lipopolysaccharide content.

4c. Drugs Used in the Recipient

Transplantation does not require and avoids the need for cytotoxic agents to suppress the immune system. Such agents are able to enter the alginate microcapsule and cause islet toxicity, as well as causing systemic toxicity. Instead, nicotinamide and a special diet are used (for rationale, see section 1.4 below).

The transplantation procedures of our earlier patent specification have the ability over a period prior to rejection of providing porcine insulin. In this respect, we ourselves conducted clinical trials.

Four type 1 diabetic adolescents received 10,000 free islets/kg bodyweight by intraperitoneal injection. The islets were located from term piglets using the standard collagenase digestion, purification and culture techniques described in section 3.2. All four recipients received oral nicotinamide (1.5 g/day) and a casein-free as herein defined diet both pre- and post-transplantation. A prompt reduction in insulin requirements, which was not clearly dose-related, was noted in the first week after transplantation. The reduction in insulin dosage range from 21 to 32%, and the response lasted for up to 14 weeks. However, insulin doses subsequently returned to their previous levels.

The most likely reason for the transplant failure in these patients was chronic rejection.

However, no adverse effects were noted.

We have now shown alginate-encapsulated porcine islet cell transplants in two human diabetic patients, prolonged functioning of the transplants. The islets were transplanted by intraperitoneal injection, one patient receiving 15,000 IEQ/kg (total 1,300,000 islets) and the other 10,000 IEQ/kg (total 930,000 islets). Both patients were treated pre- and post-transplantation with oral nicotinamide and a soy-based/casein-free as herein defined diet.

The preferred procedure as shown in FIG. 1 was used for the preparation, the encapsulation being as aforesaid. Islet cells of −7 days to +10 days fill gestation were used.

DESCRIPTION OF THE DRAWINGS

Preferred forms of the present invention or examples of working will now be described with reference to the accompanying drawings in which.

5. EXAMPLES

5a. Examples of Use of IgF-1

Figure 1:
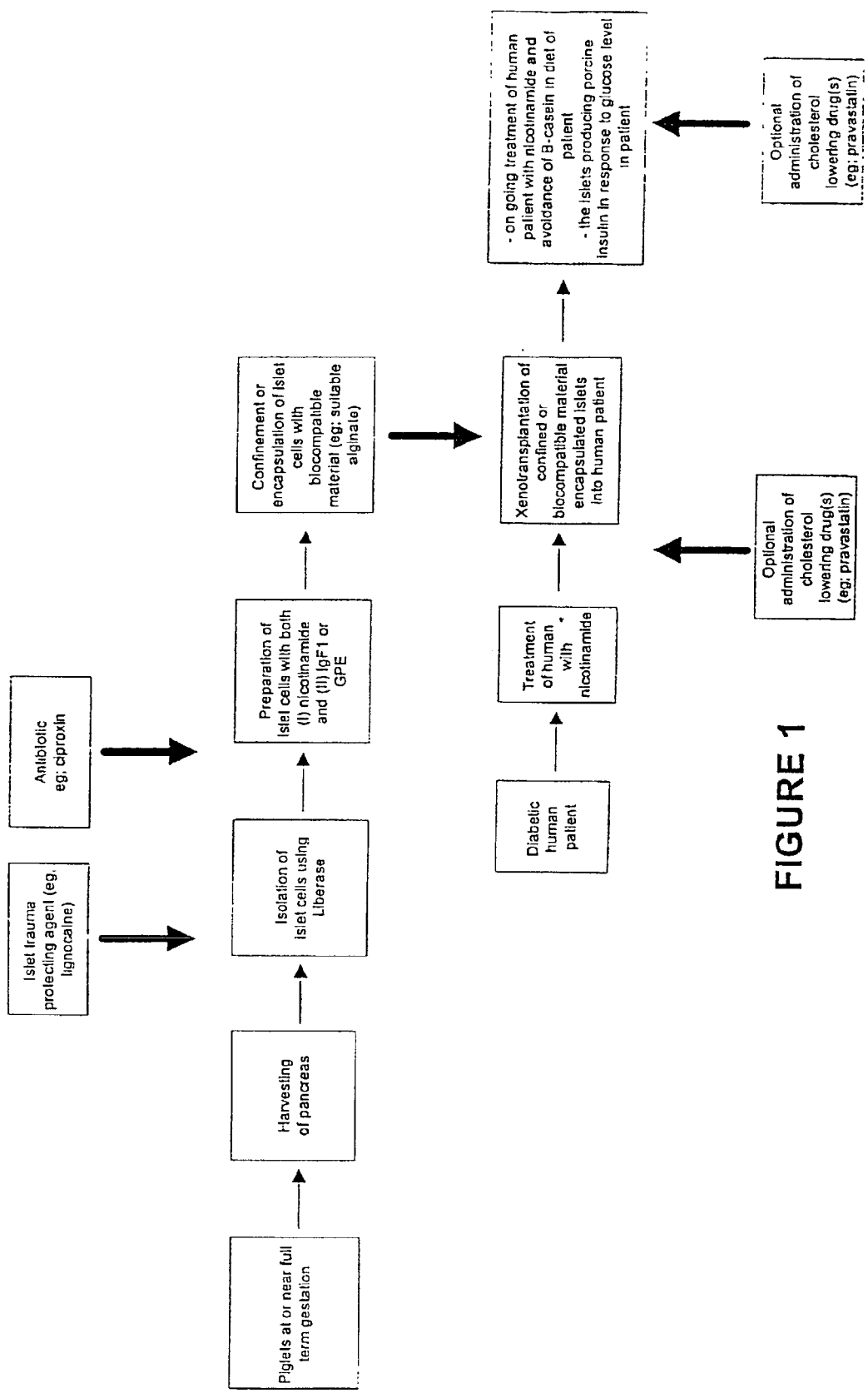
FIG. 1 shows a preferred procedure for harvesting, isolating and preparing islet cells (with either confinement or encapsulation) and the associated treatment regime for a diabetic human patient in order to receive ongoing benefit from the xenotransplantation.
Figure 2:
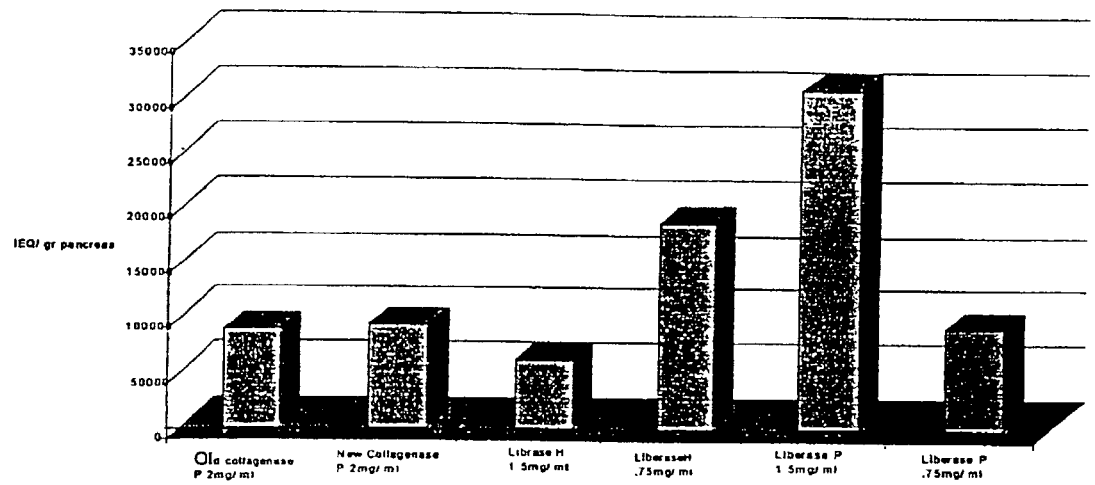
FIG. 2 shows the effect of collagenase from various sources on islet yield and function.
Figure 3:
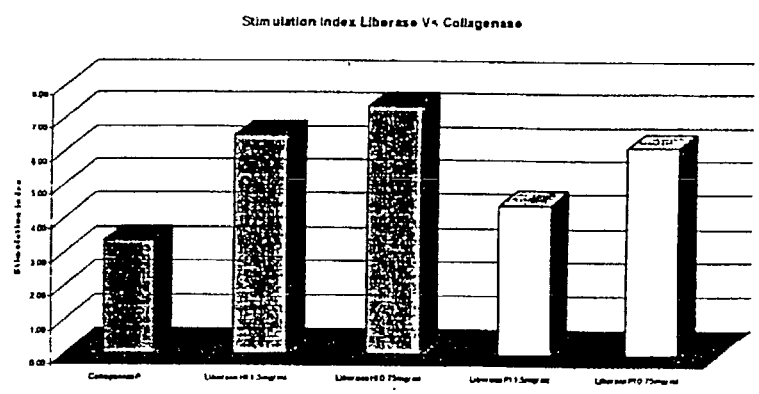
FIG. 3 shows the stimulation index of Liberase® against Collagenase clearly showing that Liberase® preparations (both human and porcine at suitable concentrations) gave higher yields and function in vitro than an optimised concentration of Collagenase P.

*Note: in the following, different experiments used different islet preparations so control values vary.

porcine islets in culture which were exposed to IgF-1, increased their insulin response to glucose, by up to a 3-fold increase.

| | Incubated 24 hrs with 0.1 ug/ml IgF-1 after isolation | CONTROL-no IgF-1 |
|---|---|---|
| Insulin secretion In response to 19.4 mM Glucose + 10 mM Theophylline After 3 days culture Post isolation | 236 uU/hr/100 IEQ | 75.2 uU/hr/100 IEQ |

A concentration of 0.1 ug/ml IgF-1 in culture is sufficient to produce optimal insulin secretion during glucose challenge. No further benefit was achieved by increasing the concentration of IgF-1.

| | Incubated 24 hrs with 0.1 ug/ml IgF-1 | Incubated 24 hrs with 1.0 ug/ml IgF-1 |
|---|---|---|
| Insulin secretion In response to 19.4 mM Glucose + 10 mM Theophylline After 3 days culture Post isolation | 58 uU/hr/100 IEQ | 56.8 uU/hr/100 IEQ |

Variations on the duration of IgF-1 exposure were tried on the porcine islet cells. However no increased benefit was found on culturing the islets with IgF-1 beyond a 24 hrs period, post isolation.

| | Incubated 7 days With 0.1 ug/ml IgF-1 | Incubated 24 hrs with 1.0 ug/ml IgF-1 |
|---|---|---|
| Insulin secretion In response to 19.4 mM Glucose + 10 mM Theophylline 7 days post isolation | 58 uU/hr/100 IEQ | 57.5 uU/hr/100 IEQ |

This increased insulin production persisted to 14 days post IgF-1 exposure. Longer durations are yet to be investigated.

| | 14 days post IgF-1 Exposure | 3 days post IgF-1 Exposure |
|---|---|---|
| Insulin secretion In response to 19.4 mM Glucose + 10 mM Theophylline | 1.3-fold increase Compared to control | 1.5-fold increase Compared to control |

Withdrawal of Nicotinamide from the culture media eliminated the benefit of IgF-1 on islet insulin production.

| | Incubated 3 days With 0.1 ug/ml IgF-1 Without Nicotinamide | Incubated 3 days With culture Media Without Nicotinamide |
|---|---|---|
| Insulin secretion In response to 19.4 mM Glucose + 10 mM Theophylline After 3 days culture Post isolation | 47.6 uU/hr/100 IEQ | 55.9 uU/hr/100 IEQ |

A concentration of 0.1 ug/ml IgF-2 during culturing appeared to increase insulin production of porcine islet cells, after an initial exposure of 24 hrs. However, this increase was transient to 3 days post exposure.

| | Incubated 24 hrs With 0.1 ug/ml IgF-2 day 1. | Control |
|---|---|---|
| Insulin secretion In response to 19.4 mM Glucose + 10 mM Theophyline After 3 days culture Post isolation | 105.8/100 IEQ | 75.2 r/100 IEQ |
| Insulin secretion In response to 19.4 mM Glucose + 10 mM Theophyline After 3 days culture Post isolation | 32 uU/hr/100 IEQ | 39.8 uU/hr/100 IEQ |

Prolonged exposure to IgF-2 beyond 24hrs, failed to increase the insulin production of the islet cells in response to glucose.

|                                                                              | Incubated 24 hrs With 0.1 ug/ml IgF-2 day 1. | Control       |
| ---------------------------------------------------------------------------- | -------------------------------------------- | ------------- |
| Insulin secretion In response to 19.4 mM Glucose + 10 mM Theophyline After 3 days culture Post isolation | 105.8/100 IEQ                                | 75.2 r/100 IEQ |

|                                                                              | Incubated 7 days With 0.1 ug/ml IgF-2 | Control          |
| ---------------------------------------------------------------------------- | ------------------------------------- | ---------------- |
| Insulin secretion In response to 19.4 mM Glucose + 10 mM Theophyline After 7 days culture Post isolation | 38.4 uU/hr/100 IEQ                    | 39.8 uU/hr/100 IEQ |

5b. Effect of N-Terminal Tripeptide (GPE) of Insulin like Growth Factor (IGF-1) on the Function of Neonatal Porcine Islet Cells.

GPE is a tripeptide (gly-pro-glu) derived from IGF-1. It is a novel neuroactive peptide with a potent effect on acetylcholine and dopamine release in cortical slices. Previous studies done using GPE support the concept that the proteolytic products of the IGF-1 precursor play a role in the regulation of brain functions.

The aim of this example was to present the effect of GPE on the function of isolated porcine islets in vitro.

Method
  Islet cell isolation with 2 pancreases;
  Isolation following the previously discussed protocol;
  RPMI media added with Ciproxin, nicotinamide, Human serum albumin
  GPE, IGF1 (1–3), Bachem A G, Lot No.0538925, stock solution of 100 ug/ml (in water): dilute farther in RPMI medium to the final concentrations: 1 ug/ml (1:100), 0.1 ug/ml (1:1000)and0.0ug/ml (1:10 000)
  1. GPE 0.01 ug/ml
  2. GPE 0.1 ug/ml
  3. GPE 1.0 ug/ml
  Keep the cells 3 days in culture before Static Glucose Stimulation (SGS). SGS involves exposure of the cells to low and high concentration of glucose to check insulin production. Using 0.1 ug/ml concentration add GPE to two plates 24 hours before SGS (day 2 after isolation)

Results of Example Sb

Exposure of neonatal porcine islets in culture to GPE increased the insulin response to glucose up to 11.5 compared with the control cells.(Stimulation Index control 13.3 compared to 24.8 when GPE was used) Viability of the cells was >85% DTZ, AO/PI staining)

Figure 5:
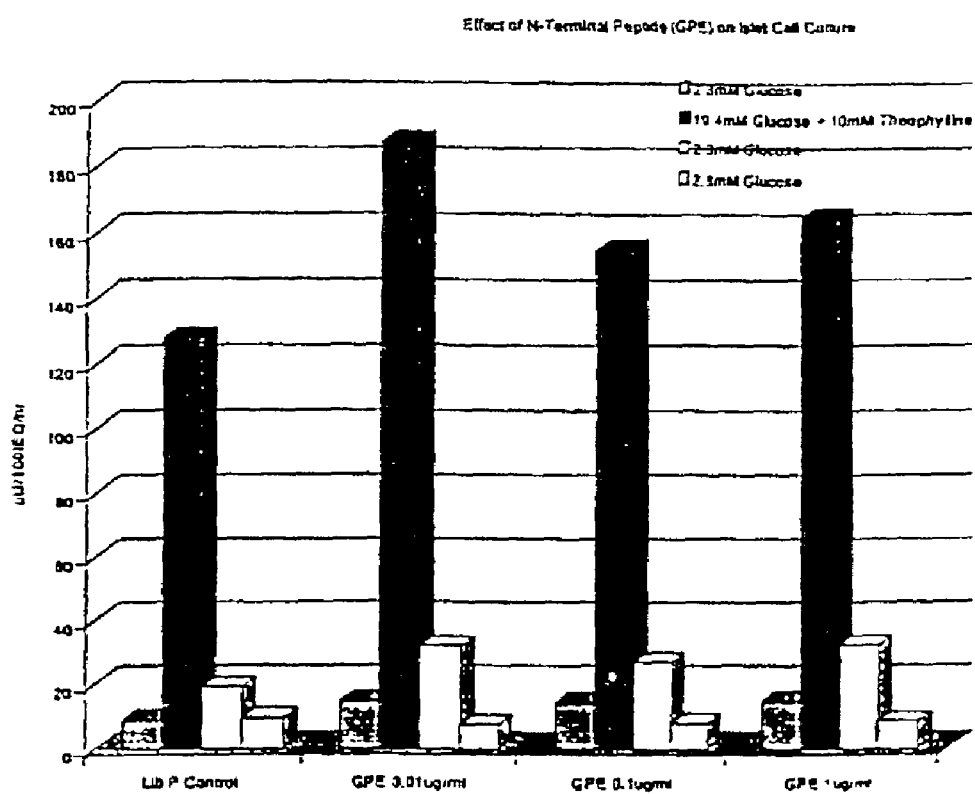
FIG. 5 shows the results of exposure of neonatal porcine islets in culture with GPE in comparison with control cells.

A concentration of 0.1 ug/ml of GPE in culture is sufficient to produce optimal response during glucose challenge. No further benefit was achieved by increasing the concentration of GPE in culture. See FIG. 5 below.

The results suggest that GPE could be used during porcine islet cell culture to improve the quality and function of the cells before transplantation. Furthermore GPE is a novel neuroactive peptide found in human brain.

5c. Examples of the Effect of Lignocaine when Used During Porcine Pancreatic Digestion, on Islet Yield and Viability.

Lignocaine is a membrane stabiliser and phospholipase A2 inhibitor. When used at a 1 mM concentration during Collagenase digestion of 7d old porcine pancreas, a 2-fold increase in islet yield is produced.

Islet endocrine function was assessed after 3 days in culture via static glucose stimulation. Islets isolated with Lignocaine during digestion produced a 3-fold increase in insulin secretion in response to glucose challenge.

|                                                                              | Collagenase alone  | Collagenase + 1 mM Lignocaine |
| ---------------------------------------------------------------------------- | ------------------ | ----------------------------- |
| Average islet yield                                                          | 40,960 IEQ/g       | 88,183 IEQ/g                  |
| Insulin secretion in response to 19.4 mM Glucose + 10 mM Theophyline After 3 days culture Post isolation | 46.4 uU/hr/100 IEQ | 163.8 uU/hr/100 IEQ           |

Conclusion: The use of Lignocaine during pancreatic digestion increases the insulin production/g of pancreas by 6-fold.

5d. Examples of the Effects of Ciproxin on Islet Function as Assessed by Static Glucose Stimulation.

Freshly prepared neonatal pig islets were prepared by standard isolation procedure and cultured for two days in RPMI medium with standard additions.

Streptomycin (100 mcg/ml)and Penicillin (100 U/ml) were included in one flask and Ciproxin (3 mcg/mi) in another.

The islets were harvested and an aliquot subjected to stimulation with theophylline and high glucose.

Figure 4:
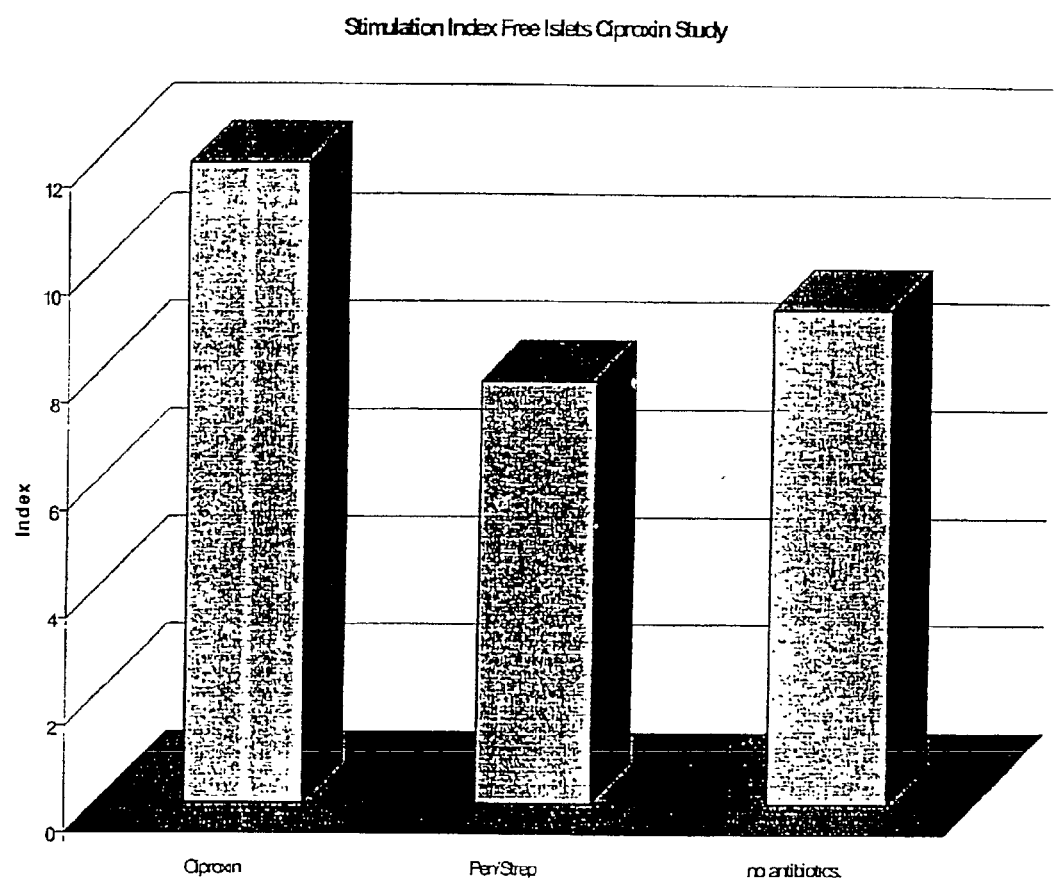
FIG. 4 shows the stimulation index of free islets when comparing the use of ciproxin against a penicillin/streptomycin mix and against a control of no antibiotics.

The comparative insulin release from the islets—a measure of viability is shown in FIG. 4.

5e. Examples of the Effects of Collagenase from Various Sources on Islet Yield and Function Pancreases of neonatal piglets aged 7 days were obtained as above and islets extracted by the same process, varying only the source and amount of collagenase. The yield/gram of pancreas is shown in the Figure.

Islets extracted using these variations in collagenase source and amount were assessed for viability using propidium iodide and dithizone for insulin content.
  DTZ staining >85%
  AO/PI >85%

The islets were then assessed for functionality by static glucose stimulation as above. The all results are shown in the Figure below.

It is apparent that the Liberase® preparations at suitable concentrations gave higher yields and function in vitro than the previously optimised concentration of Collagenase P.

5f. Examples of the Comparative Effectiveness of Islets Prepared with Liberase P or H in vivo Islets prepared with the best concentration of Liberase® P and H in this way were injected intraperitoneally into CD1 mice made diabetic by intravenous streptozotocin. The dose used was 10 islets/g body weight of mouse. Ten days after such treatment the number of mice no longer diabetic was assessed.

1/7 of the mice treated with the islets isolated with Liberase® P and 4/7 of those isolated with Liberase H were non diabetic.

Similar experiments were performed using spontaneously diabetic NOD mice. Of the surviving mice at 10 days after transplantation 3/7 of the Liberase P treated islets and 3/3 of the Liberase H islets were no longer diabetic 5g. Example of Islet Encapsulation Procedure The novel medium size microcapsules (300–400μ MSM) are prepared by atomizing the islet-alginate suspension through a special microdroplet generator.

Sodium alginate used for this procedure is extracted form raw material sources (seaweed) and prepared in powdered ultrapure form (Keltone LVCR).

The encapsulation procedure involves extruding a mixture of islets and sodium alginate solution (1.6%) through a droplet generating needle into a bath of gelling cations (calcium chloride). The islets entrapped in the calcium-alginate gel are then coated with positively charged poly-L-ornithine followed by an outer coast of alginate (0.05%). The central core of alginate is then liquified by the addition of sodium citrate. Most capsules contain 3 islets and have a diameter of 300 to 400 μm.

The encapsulated islets are kept in cell culture, and then checked for contamination, insulin release and viability before transplantation.

DEFINITIONS

As used herein:

"Administering" includes self-administering;

"Casein-free" when referring to milk as used herein refers to milk which does not contain a diabetogenic factor, particularly to milk containing no variant of β-casein which stimulates diabetogenic activity in humans. With reference to International PCT Application WO 96/14577, a non-diabetogenic variant for example, may be the A2 variant of β-casein. The full contents of PCT/NZ95/00114 (WO 96/14577) and PCT/NZ96/00039 (WO 96/36239) are here included by way of reference.

"Casein-free" as used herein in respect of dietary considerations means at least a substantial avoidance (preferably total avoidance) of such milk containing or derived diabetogenic factors.

IgF1 is Human Insulin-like Growth Factor I and is a potent mitogenic growth factor that mediates the growth promoting activities of growth hormone postnatally. Both IGF-1 and IGF-2 are expressed in many cell types and may have endocrine, autocrine and paracrine functions.

The N-terminal tripeptide of Ig F-1 or "GPE" is the amino-terminal tripeptide glycine-proline-glutamate of IGF-1.

"mammalian albumin" as used herein means serum albumin from mammals, preferably human serum albumin (HSA).

"appropriate collagenase" means preferably Liberase® , ideally human or porcine, ideally Liberase H®.

"mechanically reduced" as used herein includes any process where pancreatic tissue is increased in surface area eg, mechanical or water jet shredding, grinding, mincing, etc . . .

The invention claimed is:

1. A method of preparing a xenotransplantable islet comprising in sequential order the steps of:
   (i) harvesting the pancreas of a piglet, said piglet having an age of between −20 to +10 days relative to full-term gestation,
   (ii) exposing said harvested pancreas to nicotinamide,
   (iii) exposing said harvested pancreas to lignocaine; and
   (iv) extracting pancreatic β islet cells from said harvested pancreas and simultaneously contacting said pancreatic β islet cells with a quinolone antibiotic, wherein said method results in said xenotransplantable islet.

2. A method of preparing a xenotransplantable porcine islet, said method comprising in sequential order at least the steps of:
   (i) harvesting a pancreas of a piglet, the piglet having an age of between −20 to +10 days relative to full-term gestation,
   (ii) exposing said harvested pancreas to nicotinamide, and
   (iii) extracting pancreatic β islet cells from said harvested pancreas and simultaneously contacting said pancreatic β islet cells with ciprofloxacin; wherein said method results in said xenotransplantable porcine islet.

3. A method of preparing a xenotransplantable porcine islet, said method comprising in sequential order at least the steps of:
   (i) harvesting a pancreas of a piglet, said piglet having an age of between −20 to +10 days relative to full-term gestation,
   (ii) exposing said harvested pancreas to nicotinamide, and
   (iii) extracting pancreatic β islet cells from said harvested pancreas and simultaneously contacting said pancreatic β islet cells with lignocaine, wherein said method results in said xenotransplantable porcine islet.

4. A method of preparing a xenotransplantable porcine islet comprising in sequential order the steps of:
   (i) harvesting the pancreas of a piglet, the piglet having an age of between −20 to +10 days relative to full-term gestation,
   (ii) exposing said harvested pancreas to nicotinamide,
   (iii) exposing said harvested pancreas to ciprofloxacin; and
   (iv) extracting pancreatic β islet cells from said harvested pancreas and simultaneously contacting said pancreatic β islet cells with a trauma-protecting agent, wherein said method results in said xenotransplantable islet.

5. A method of preparing a xenotransplantable porcine islet, comprising in sequential order the steps of:
   (i) harvesting the pancreas of a piglet, the piglet having an age of between −20 to +10 days relative to full term gestation,
   (ii) exposing the harvested pancreas to a trauma-protecting agent lignocaine,
   (iii) exposing the harvested pancreas to nicotinamide, and
   (iv) extracting pancreatic β islet cells from the harvested pancreas and simultaneously contacting the pancreatic β islet cells with a quinolone antibiotic; the method resulting in a xenotransplantable islet.

6. A method of preparing a xenotransplantable porcine islet comprising in sequential order the steps of:
   (i) harvesting the pancreas of a piglet, the piglet having an age of between −20 to +10 days relative to full term gestation,
   (ii) exposing the harvested pancreas to the quinolone antibiotic ciprofloxacin,
   (iii) exposing the harvested pancreas to nicotinamide, and
   (iv) extracting pancreatic β islet cells from the harvested pancreas and simultaneously contacting the pancreatic β islet cells with a trauma protecting agent lignocaine; the method resulting in a xenotransplantable islet.

7. A method of preparing a xenotransplantable porcine islet comprising in sequential order the steps of:

(i) harvesting the pancreas of a piglet, said piglet having an age of between −20 to +10 days relative to full-term gestation;
(ii) exposing said harvested pancreas of said piglet to nicotinamide;
(iii) exposing said harvested pancreas to lignocaine;
(iv) extracting pancreatic β islet cells from said harvested pancreas in the presence of a suitable collagenase; and
(v) contacting said extracted pancreatic β islet cells with a quinolone antibiotic, wherein said method results in the preparation of said xenotransplantable porcine islet.

8. A method of preparing a xenotransplantable porcine islet comprising in sequential order the steps of:
(i) harvesting the pancreas of a piglet, said piglet having an age of between −20 to +10 days relative to full-term gestation;
(ii) exposing said harvested pancreas of said piglet to nicotinamide;
(iii) exposing said harvested pancreas to a trauma-protecting agent;
(iv) extracting pancreatic β islet cells from said harvested pancreas in the presence of a suitable collagenase; and
(v) contacting said extracted pancreatic β islet cells with the quinolone antibiotic ciprofloxacin, wherein said method results in the preparation of said xenotransplantable porcine islet.

9. The method of any one of claims 1–4, wherein the piglet has an age of between −7 and +10 days relative to full term gestation.

10. The method of any one of claims 1–4, wherein the step of extraction includes the use of a suitable human collagenase.

11. The method of any one of claims 1–4, wherein the harvested pancreas is bathed in a mammalian albumin solution substantially free of microbiological agents.

12. The method of any one of claim 11, wherein the mammalian albumin comprises human serum albumin (HSA).

13. The method of any one of claims 1–4, further comprising a step of contacting the β islet cells with a compound selected from the group consisting of insulin-like growth factor 1 (IGF-1) and the N-terminal tripeptide of IGF-1.

14. The method of claim 13, wherein the compound consists of the N-terminal tripeptide of IGF-1.

15. The method of claim 4, wherein the trauma protecting agent comprises an anesthetic agent.

16. The method of claim 15, wherein the anesthetic agent comprises a phospholipase A2 inhibitor.

17. The method of claim 16, wherein the phospholipase A2 inhibitor comprises lignocaine.

* * * * *